(12) United States Patent
DeBellis et al.

(10) Patent No.: US 7,268,235 B2
(45) Date of Patent: Sep. 11, 2007

(54) METHOD FOR PREPARATION OF N-PYRAZOLYLAMIDOXIMES

(75) Inventors: Francesco DeBellis, Rochester, NY (US); Chang-Kyu Kim, deceased, late of Pittsford, NY (US); by Alice J. Kim, legal representative, New York, NY (US)

(73) Assignee: Eastman Kodak Company, Rochester, NY (US)

( * ) Notice: Subject to any disclaimer, the term of this patent is extended or adjusted under 35 U.S.C. 154(b) by 534 days.

(21) Appl. No.: 10/954,875

(22) Filed: Sep. 30, 2004

(65) Prior Publication Data

US 2006/0074245 A1 Apr. 6, 2006

(51) Int. Cl.
*C07D 231/10* (2006.01)
(52) U.S. Cl. .................. 548/371.7; 548/125; 548/131; 548/356.1; 548/371.4
(58) Field of Classification Search ................. 548/125, 548/131, 356.1, 371.4, 371.7
See application file for complete search history.

(56) References Cited

FOREIGN PATENT DOCUMENTS

GB 626470 7/1949

OTHER PUBLICATIONS

Merckx, Raymond, 1,2,4-Oxidiazole derivatives, Bulletin des Societes Chimiqus Belges (1949), pp. 58-65 with abstract.

Harry L. Yale, et al., "3,5-Disubstituted-1,2,4-oxadiazoles and 4,5-Dihydro-3,5-disubstituted-1,2,4-oxadiazoles", J. Heterocyclic Chem., vol. 15, 1978, pp. 1373-1378.

*Primary Examiner*—Golam M. M. Shameem
(74) *Attorney, Agent, or Firm*—Arthur E. Kluegel

(57) ABSTRACT

A method for the preparation of N-pyrazolylamidoximes of the general formula I

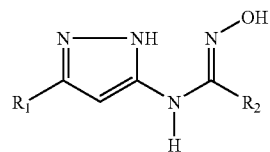

Formula I $R_1$ and $R_2$ independently represent an alkyl, aryl, or heteroaryl group, comprises reacting a 5-(β-ketoalkyl)-3-substituted-1,2,4-oxadiazoles of the general formula II

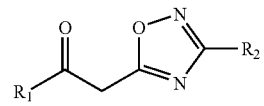

Formula II with hydrazine.

34 Claims, No Drawings

METHOD FOR PREPARATION OF N-PYRAZOLYLAMIDOXIMES

CROSS REFERENCE TO RELATED APPLICATION

This application is being cofiled with an application Ser. No. 10/955,347 entitled OXADIAZOLES AND THEIR MANUFACTURE.

FIELD OF THE INVENTION

This invention relates to a method for preparation of N-pyrazolyl-amidoximes, precursors of 1H-pyrazolo[1,5-b]-1,2,4-triazole magenta couplers for color photography.

BACKGROUND OF THE INVENTION

A new class of magenta-dye forming couplers used-lately in color photography is 1H-pyrazolo[1,5-b]-1,2,4-triazole couplers. Image dyes formed from these couplers have an excellent light fastness. Examples are couplers disclosed in U.S. Pat. No. 4,540,654; U.S. Pat. No. 4,621,046; U.S. Pat. No. 4,882,266; U.S. Pat. No. 5,262,542; U.S. Pat. No. 5,378,587; U.S. Pat. No. 5,451,501, JP 60-197688; and JP 03-184980. The couplers have a unique 5/5 heterocyclic ring system. It has been built with no exception from a 3-ketopropionitrile (1) as shown in the following scheme:

There are several disadvantages, however, in the preparation of a 1H-pyrazolo[1,5-b]-1,2,4-triazole using 3-aminopyrazole (2) as a key intermediate (1) A 3-ketopropionitrile (1) is not readily available. It is usually prepared from a commercially available precursor like a α-halo ketone by replacing halogen with cyanide. Such a replacement reaction with cyanide is difficult and has a lot of disadvantages in environment, safety, health, and cost issues.

(2) A 3-aminopyrazole (2) is known to be highly toxic, and no chemical regulatory clearance work has been done in U.S. and Europe. Its use as a raw material requires lots of upfront cost. It is another significant disadvantage in the issues of environment, safety, health, and cost.

(3) Down-stream chemistry from 3-aminopyrazole (2) is inflexible. It has to be reacted with an imidate ester such as 4 in the next step. Most of imidate esters are so sensitive to water that they should be used in a strictly anhydrous medium. Any amount of water present causes formation of an amide that is not reactive at all in subsequent reactions. Reaction of a 3-aminopyrazole and an imidate ester gives either N-pyrazolyl-amidine or N-pyrazolyl-imidate dependent upon pH of medium. Either one of these intermediates can be transformed to N-pyazolylamidoxime in subsequent step. It is difficult, however, to get either one of the intermediates cleanly, so that it is used without isolation in the next step. The next step reaction requires free hydroxy-

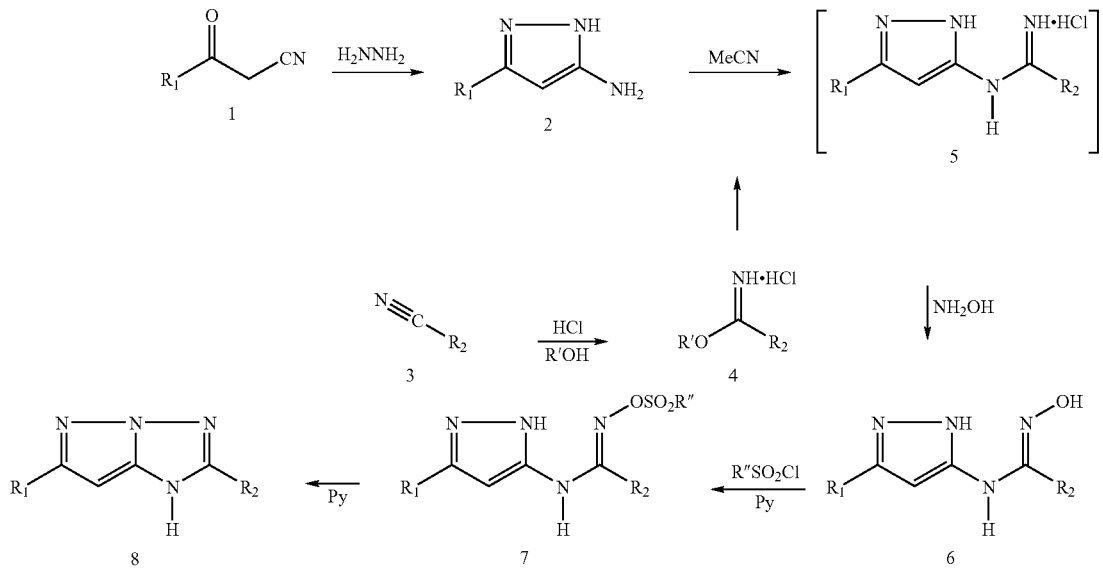

Reaction of a 3-ketoprionitrile (1) with hydrazine gives a 3-aminopyrazole (2). A 3-aminopyrazole (2) is then reacted with an alkyl or aryl imidate ester hydrochloride (4) to give a N-pyrazolylamidine (5). An imidate ester hydrochloride (4) can be prepared by addition of an alcohol (R'OH) and hydrochloride to an alkyl or aryl nitrile (3). A N-pyrazolylamidine (5) can be converted to a N-pyrazolylamidoxime (6) by a reaction with hydroxylamine. O-Sulfonation of a N-pyrazolylamidoxime (6) with alkyl- or aryl-sulfonyl chloride (R''SO$_2$Cl) followed by ring closure gives a 1H-pyrazolo[1,5-b]-1,2,4-triazole (8). In this synthetic sequence 3-aminopyrazole (2) is a key intermediate for making a 1H-pyrazolo[1,5-b]-1,2,4-triazole coupler.

lamine that is liberated from commercially available salt form. It often requires a strong organic base such as triethylamine, 1,5-diazabicyclo[4,3,0]non-5-ene, or 1,8-diazabicyclo[5,4,0]-undec-7-ene, which is costly and causes difficulties in waste disposal. It is a disadvantage in environment, flexibility, and cost issues.

(4) The overall process described above is so complicated and dependent upon dryness of the medium that it gives a highly variable result. It is a disadvantage in the issues of consistency, yield, and cost.

It is therefore desirable to develop a simpler, environmentally friendlier, less toxic and low-cost process for preparation of N-pyrazolyl-amidoxime, a key intermediate for 1H-pyrazolo[1,5-b]-1,2,4-triazole magenta dye-forming couplers.

SUMMARY OF THE INVENTION

The present invention provides a method for the preparation of N-pyrazolylamidoximes of the general formula I

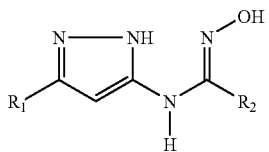

Formula I

R$_1$ and R$_2$ independently represent an alkyl aryl, or heteroaryl group, comprises reacting a 5-(β-ketoalkyl)-3-substituted-1,2,4-oxadiazoles of the general formula II

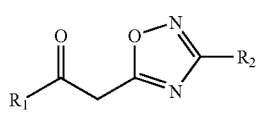

Formula II with hydrazine.

DETAILED DESCRIPTION OF THE INVENTION

In formula I, R$_1$ and R$_2$ independently represent a substituent group in the art which promotes solubility, diffusion resistance, dye hue, or dye stability of the dye formed upon reaction of the coupler with the oxidized color developing agent. Representative R$_1$ and R$_2$ groups include alkyl, aryl, or heteroaryl groups having 1-40, particularly 1-30, carbon atoms, which may be unsubstituted or substituted with one or more substituents that do not adversely affect the preparation and use of the intermediate. Examples of such substituents include a halogen, nitro, cyano, carboxy, hydroxy, alkyl, aryl, heteroaryl, alkoxy, aryloxy, alkylthio, arylthio, alkyl amino, arylamino, alkoxycarbonyl, aryloxycarbonyl, acyl, acyloxy, acylamino, acylimino, carbonamido, carbamoyl, alkylsulfonyl, arylsulfonyl, sulfonamido, and sulfamoyl groups wherein the alkyl and aryl substituents, and the alkyl and aryl portions of the alkoxy, aryloxy, alkylthio, arylthio, alkylamino, arylamino, alkoxycarbonyl, aryloxycarbonyl, acyl, acyloxy, acylamino, acylimino, carbonamido, carbamoyl, alkylsulfonyl, arylsulfonyl, sulfonamido, and sulfamoyl substituents contain 1-30 carbon atoms and 6-30 carbon atoms, respectively, and can be farther substituted with such substituents.

Preferred R$_1$ group include: a straight chain alkyl group such as metyl, ethyl, propyl, butyl, pentyl, hexyl, heptyl, octyl, nonyl, decyl, undecyl, dodecyl, tridecyl, tetradecyl, pentadecyl, heptadecyl, octadecyl, or nonadecyl; a branched alkyl group such as isopropyl, sec-butyl, t-butyl, 1-ethylbutyl, t-pentyl, 2-ethylhexyl, or 2-hexyloctyl; a cyclic alkyl group such as cyclopropyl, cyclobutyl, cyclopentyl, cyclohexyl, 1-methylcyclopropyl, 1-methylcyclobutyl, 1-methylcyclopentyl, 1-methylcyclo-hexyl, or adamentyl; an arylalkyl group such as phenylmethyl, 4-chlorophenyl-methyl, 4-methoxyphenylmethyl, 4-nitrophenyl-methyl, 2-(4'-nitrophenyl)ethyl, or 3-(4'-nitrophenyl)propyl; an aryloxyalkyl group such as phenoxymethyl, 4-nitrophenoxymethyl, 2-(4-nitrophenoxy)ethyl, 3-(4-nitrophenoxy)propyl, 2,4-di-t-pentylphenoxymethyl, 1-(2,4-di-t-pentyl-phenoxy)propyl, 1-(2,4-di-t-pentylphenoxy)pentyl, 3-pentadecylphenoxymethyl, 1-(3-pentadecylphenoxy)-propyl, 1-(4-butylsulfonylaminophenoxy)tridecyl, or 2-octylsulfonylaminophenoxymethyl; an alkylsulfonylalkyl such as 1-dodecyl-sulfonylpropyl, 3-dodecylsulfonylpropyl, 1-dodecylsulfonylpentyl, 1-dodecylsulfonyl-2-methypropyl, 1-tetradecylsulfonylpropyl, or 1-hexadecylsulfonylpropyl; an arylsulfonylalkyl such as 1-(4-dodecyloxybenzenesulfonyl)propyl, or 1-(4-hexadecyloxybenzenesulfonyl)propyl; an aryl group such as phenyl, 4-chloro-phenyl, 2-methoxyphenyl, 4-methoxyphenyl, 4-nitrophenyl, 4-dodecyloxyphenyl, or 4-hexadecyloxyphenyl; and a heteroaryl such as 2-furyl, 3-pyridyl, or 3-quinolinyl.

Preferred R$_2$ groups include a substituted alkyl such as chloromethyl, 1-bromopropyl, 1-bromopentyl, 1-bromo-2-methylpropyl, 1-bromotridecyl, nitro-methyl, cyanomethyl, 4-nitrophenylmethyl, 4-nitrophenylpropyl, 4-nitrophenoxymethyl, 1-(4-nitrophenoxy)propyl, 1-(4-nitrophenoxy)pentyl, 1-(4-nitrophenoxy)-2-methylpropyl, 1-(4-nitrophenoxy)-tridecyl, 1-(4-butylsulfonylaminophenoxy)-tridecyl, 3-(4-nitrophenoxy)propyl, 2-phthalimidoethyl, 1-methyl-2-phthalimido-ethyl, ethoxycarbonylmethyl, 1-dodecylsulfonylpropyl, 1-dodecylsulfonyl-2-methylpropyl, 1-tetradecylsulfonyl-propyl, 1-hexadecylsulfonylpropyl, 1-(4-dodecyloxyphenylsulfonyl)propyl, 1-(4-hexadecyloxyphenylsulfonyl)propyl, or 2-octylsulfonylaminophenoxymethyl; a substituted aryl group such as 2-nitrophenyl, 3-nitrophenyl, 4-nitrophenyl, 4-chloro-3-nitrophenyl, 2-butoxy-5-nitrophenyl, 4-ethoxycarbonylphenyl, 3-do-decyloxyphenyl, 4-dodecyloxyphenyl, 4-tetradecyloxyphenyl, 4-hexadecyloxy-phenyl, or 2-(4-t-butylphenoxy)-5-nitrophenyl; and a substituted heteroaryl group such as 5-nitro-2-furyl, 2-butoxy-3-pyridyl, or 5-nitro-3-pyrazolyl.

The inventive method comprises reaction of a 5-(β-ketoalkyl)-3-substituted-1,2,4-oxadiazole (Formula II) with hydrazine to give a N-pyrazolyl-amidoxime (Formula I) as illustrated in the following scheme:

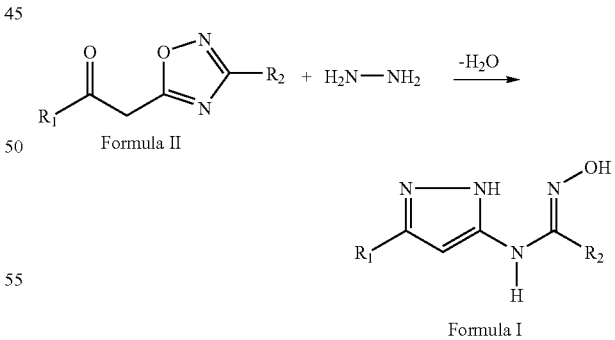

The reaction of a 5-(β-ketoalkyl)-3-substituted-1,2,4-oxadiazole (Formula II) with hydrazine to give a N-pyrazolylamidoxime (Formula I) is simple and straightforward. In the reaction, O-ketoalkyl portion forms a hydrazone and then cyclizes to form a pyrazole and open up oxadiazole ring. The reaction requires an excess of hydrazine and an elevated temperature. Preferred amount of hydrazine is 1.05-2.5 eq. and preferred temperature is 25-200° C. The reaction is carried out in an organic solvent or solvent mixture. Preferred solvents include: an alcoholic solvent such as methanol, ethanol, propyl alcohol, isopropyl alcohol, or n-butyl alcohol; a hydrocarbon solvent such as hexane, heptane, toluene, or xylene; an ethereal solvent such as di-isopropyl ether, tetrahydrofuran, or dioxane; an ester such as ethyl acetate, propyl acetate, or ethyl propionate; an organic acid such as formic acid, acetic acid, propionic acid, or methanesulfonic acid; and an organic base such as pyridine, N,N-di-methylaniline, triethylamine, or triethanolamine. The reaction runs with or without an acid catalyst. Preferred catalyst includes hydrochloric acid, sulfuric acid, phosphoric acid, formic acid, acetic acid, propionic acid, methanesulfonic acid, benzene-sulfonic acid, or p-toluene-sulfonic acid.

The following are examples of oxadiazoles useful in the method of the invention:

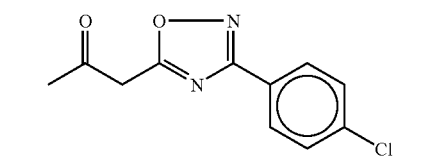

$R_1 = CH_3$
$R_2 = Ph\text{-}pCl$

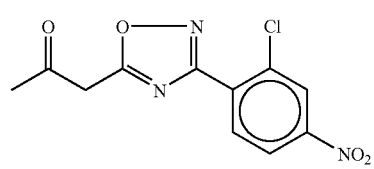

$R_1 = CH_3$
$R_2 = Ph\text{-}oCl, pNO_2$

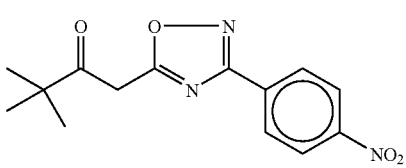

$R_1 = t\text{-butyl}$
$R_2 = Ph\text{-}pNO_2$

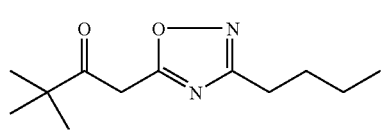

$R_1 = t\_butyl$
$R_2 = butyl$

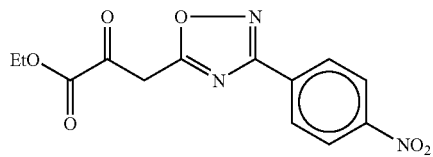

$R_1 = EtOCO$
$R_2 = Ph\text{-}pNO_2$

-continued

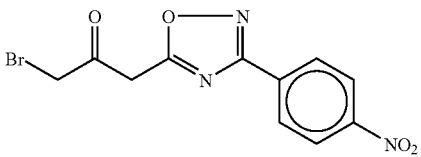

$R_1 = BrCH_2$
$R_2 = Ph\text{-}pNO_2$

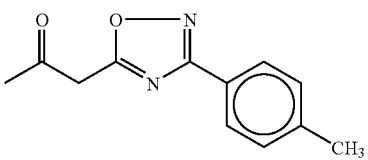

$R_1 = CH_3$
$R_2 = Ph\text{-}pCH_3$

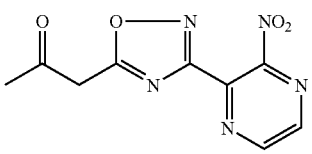

$R_1 = CH_3$
$R_2 = o\text{-nitropyrazine}$

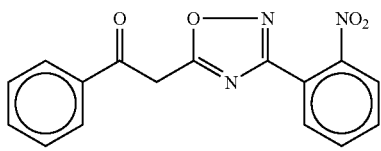

$R_1 = Phenyl$
$R_2 = Ph\text{-}oNO_2$

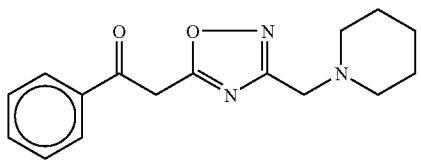

$R_1 = Phenyl$
$R_2 = 1\text{-piperidinylmethyl}$

Conversion of a N-pyrazolylamidoxime (Formula I) to a 1H-pyrazolo[1,5-b]-1,2,4-triazole (8) by O-sulfonation with alkyl- or aryl-sulfonyl chloride (R"SO₂Cl) followed by ring closure is same as the known arts described earlier.

A 5-(β-ketoalkyl)-3-substituted-1,2,4-oxadiazole (Formula II) is easily prepared by a β-keto-alkylester (10) with an amidoxime (9) and dehydrative cyclization as shown in the following scheme:

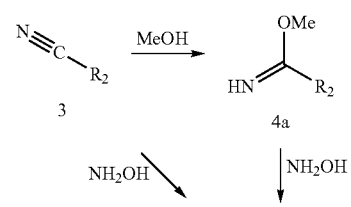

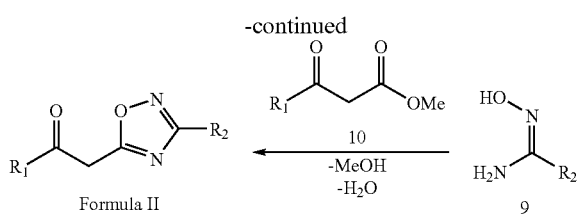

An amidoxime (9) is easily prepared from a nitrile (3). Addition of methanol to a nitrile (3) gives an imidate ester (4a) and subsequent reaction of the imidate ester with hydroxylamine gives an amidoxme (9). Some amidoximes (9) can be obtained directly from nitrile (3) by addition of hydroxylamine.

The invented method for making N-pyrazolylamidoximes (Formula I) as a precursor of 1H-pyrazolo[1,5-b]-1,2,4-triazole magenta couplers has a number of advantages over the use of 3-ketopropionitriles (1) and 3-aminopyrazoles (2) in the prior arts.

(1) A β-ketoalkylester (10) is a readily available raw material. It is usually prepared from a commercially available methyl ketone (11) by condensation with dimethylcarbonate (12) as shown in the following:

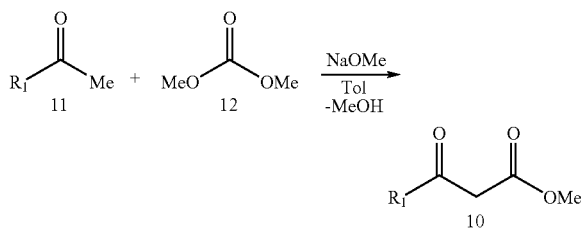

Such a condensation reaction is easy and does not impose any safety, toxicity, or environmental concern. Certain β-ketoalkylester is commercially available in a multi-ton quantity. For example, methyl 4,4-dimethyl-3-oxovalerate (10a; $R_1$=t-butyl) is a basic raw material for the preparation of many yellow dye-forming couplers, and available at a very low-cost. It is therefore a significant advantage in terms of safety, health, environment, and cost.

(2) An amidoxime (9) is also a readily available intermediate. It is easily prepared from a corresponding nitrile by addition of methalol and subsequent reaction with hydroxylamine. A nitrile that contains an electron withdrawing substituent gives amidoxime directly by simple addition of hydroxylamine. Certain amidoximes such as 3-nitrobenzamidoxime (9a; R=3-nitrophenyl) and 4-nitrobenzamidoxime (9b; R=4-nitrophenyl) are commercially available and listed in a chemical regulatory clearance list. It is another significant advantage in health, environment, and cost issues.

(3) 5-(β-Ketoalkyl)-3-substituted-1,2,4-oxadiazoles (Formula I) have no amino group attached so that they may be less toxic than 3-aminopyrazoles in prior arts. Their uses as intermediates are environmentally more favorable and require less upfront cost for chemical regulatory clearance work. It is also advantage in health, environment, and cost issues.

(4) The invented method is simple and straightforward. A simple reaction of an oxadiazole (Formula II) with hydrazine gives desired N-pyrazolyl-amidoxime (Formula I) and only by-product is water. It is thus another advantage in terms of health, environment, and cost.

The invention provides a safer, simpler, environmentally friendlier and low-cost method for preparation of N-pyrazolylamidoxime, a precursor of 1H-pyrazolo[1,5-b]-1,2,4-triazole magenta dye-forming couplers in color photography.

EXAMPLE 1

N-(5-t-Butyl)pyrazol-3-yl-3-nitrobenzamidoxime
[Formula I: $R_1$=t-butyl and $R_2$=3-nitrophenyl]

In a 500-ml flask, place 30.6 g (0.21 m) of 3-nitrobenzonitrile (3a; $R_2$=3-nitrophenyl) and 150 ml of methanol and stir to a solution. Add 48 g (0.22 m) of 25 wt % sodium methoxide in methanol slowly and stir at room temperature for 1.5 hrs. Add 22.5 ml of acetic acid to make pH of reaction mixture around 6. Add 18.1 g (0.22 m) of sodium acetate and 22 g (0.32 m) of hydroxylamine hydrochloride. After a few minutes with stirring, the reaction mixture becomes thick yellow slurries. Stir the slurries at room temperature for 1 hr. Add 130 ml of water and stir for 15 min. Collect solid, wash with water and dry in air to give 30.5 g (80%) of 3-nitrobenzamidoxime (9a; R=3-nitrophenyl).

In a 250 ml flask, place 16 g (0.088 m) of 3-nitrobenzamidoxime (9a), 21.3 g (0.135 m) of methyl 4,4-dimethyl-3-oxovalerate (10a; $R_1$=t-butyl), and 120 ml of toluene. Heat and stir the reaction mixture under reflux with a Dean-Stark trap for 23 hrs. Distill off toluene under a reduced pressure at 50-60° C. to thick oil. Add 60 ml of heptane to the oil with stirring, cool and stir at 0-5° C. for 30 min. Collect solid, wash with heptane, and dry in air to give 22.9 g (90%) of 5-(3,3-dimethyl-2-oxobutyl)-3-(3-nitrophenyl)-1,2,4-oxadiazole [Formula II: $R_1$=t-butyl and $R_2$=3-nitrophenyl].

In a 100 ml flask, place 6 g (0.0207 m) of 5-(3,3-dimethyl-2-oxobutyl)-3-(3-nitrophenyl)-1,2,4-oxadiazole [Formula II], 50 ml of isopropyl alcohol and 2.1 g (0.042 m) of hydrazine hydrate. Heat and stir the mixture under reflux for 24 hrs. Cool to room temperature, add 100 ml of water and 10 ml of concentrated hydrochloric acid, and extracted twice with 100 ml of dichloromethane each. Combine extracts, dry over magnesium sulfate, and concentrate to dryness to give 5.4 g (85%) of N-(5-t-butyl)pyrazol-3-yl-3-nitrobenzamidoxime [Formula I; $R_1$=t-butyl and $R_2$=3-nitrophenyl]

EXAMPLE 2

N-(5-methyl)pyrazol-3-yl-3 nitrobenzamidoxime
[Formula I: $R_1$=methyl and $R_2$=3-nitrophenyl]

In a 250 ml flask, place 10 g (0.055 m) of 3-nitrobenzamidoxime (9a), 9.6 g (0.083 m) of methyl acetoacetate (10b; $R_1$=methyl), and 100 ml of toluene. Heat and stir the reaction mixture under reflux with a Dean-Stark trap for 16 hrs. Distill off toluene under a reduced pressure at 50-60° C. to thick oil. Add 60 ml of heptane to the oil with stirring, cool and stir at 0-5° C. for 30 min. Collect solid, wash with heptane, and dry in air to give 11.4 g (84%) of 5-(2-oxopropyl)-3-(3-nitrophenyl)-1,2,4-oxadiazole [Formula II: $R_1$=methyl and $R_2$=3-nitrophenyl].

In a 100 ml flask, place 4.5 g (0.0182 m) of 5-(2-oxopropyl)-3-(3-nitrophenyl)-1,2,4-oxadiazole [Formula II], 50 ml of isopropyl alcohol and 1.8 g (0.036 m) of hydrazine hydrate. Heat and stir the mixture under reflux for 4 hrs. Cool to room temperature, add 100 ml of water and 10 ml of concentrated hydrochloric acid, and extracted twice with 75 ml of dichloromethane each and twice with 75 ml of ethyl acetate each. Combine extracts, dry over magnesium sulfate, and concentrate to a solid. Add 25 ml of acetonitrile, stir for a few min, collect and dry in air to give 3.1 g (65%) of N-(5-methyl)pyrazol-3-yl-3-nitrobenzamidoxime [Formula I; $R_1$=7 methyl and $R_2$=3-nitrophenyl]

EXAMPLE 3

N-(5-p-methoxyphenyl)pyrazol-3-yl-3 nitrobenzamidoxime [Formula I: $R_1$=p-methoxyphenyl and $R_2$=3-nitrophenyl]

In a 100 ml flask, place 5 g (0.0276 m) of 3-nitrobenzamidoxime (9a), 8.6 g (0.0414 m) of methyl p-methoxyphenyacetoacetate (10c; $R_1$=p-methoxyphenyl), and 50 ml of toluene. Heat and stir the reaction mixture under reflux with a Dean-Stark trap for 14 hrs. Cool the reaction mixture to room temperature, add 40 ml of heptane and stir for 30 min. Collect solid, wash with heptane, and dry in air to give 8.4 g (85%) of 5-(p-methoxyphenyl)acetyl-3-(3-nitrophenyl)-1,2,4-oxadiazole [Formula II: $R_1$=p-methoxyphenyl and $R_2$=3-nitrophenyl].

In a 100 ml flask, place 5 g (0.014 m) of 5-(p-methoxyphenyl)acetyl-3-(3-nitrophenyl)-1,2,4-oxadiazole [Formula II], 50 ml of isopropyl alcohol and 1.4 g (0.028 m) of hydrazine hydrate. Heat and stir the mixture under reflux for 8 hrs. Cool to room temperature, add 100 ml of water and 10 ml of concentrated hydrochloric acid, and extracted twice with 100 ml of dichloromethane each. Combine extracts, dry over magnesium sulfate, and concentrate to a gum. Add 50 ml of heptane, stir for 30 min, collect and dry in air to give 4.6 g (82%) of N-(5-p-methoxyphenyl)pyrazol-3-yl-3-nitrobenzamidoxime [Formula I; $R_1$=p-methoxyphenyl and $R_2$=3-nitrophenyl].

The patents and other publications cited herein are incorporated herein in their entirety. The invention has been described in detail with particular reference to certain preferred embodiments thereof, but it will be understood that variations and modifications can be effected within the spirit and scope of the invention.

The invention claimed is:
1. A method for the preparation of N-pyrazolylamidoximes of the general formula I

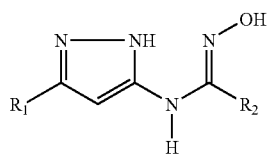

Formula I wherein $R_1$ and $R_2$ independently represent an alkyl, aryl, or heteroaryl group, comprising
reacting a 5-(β-ketoalkyl)-3-substituted-1,2,4-oxadiazoles of the general formula II

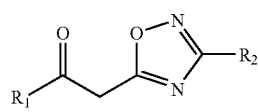

Formula II with hydrazine.

2. The method of claim 1 wherein $R_1$ is a straight chain alkyl, branched alkyl, cyclic alkyl, arylalkyl, aryloxyalkyl, alkylsulfonylalkyl, arylsulfonylalkyl, aryl, or heteroaryl group.

3. The method of claim 2 wherein $R_1$ is a straight chain alkyl group selected from methyl, ethyl, propyl, butyl, pentyl, hexyl, heptyl, octyl, nonyl, decyl, undecyl, dodecyl, tridecyl, tetradecyl, pentadecyl, heptadecyl, octadecyl, and a nonadecyl group.

4. The method of claim 2 wherein $R_1$ is a branched alkyl group selected from isopropyl, sec-butyl, t-butyl, 1-ethylbutyl, t-pentyl, 2-ethylhexyl, and a 2-hexyloctyl group.

5. The method of claim 2 wherein $R_1$ is a cyclic alkyl group selected from cyclopropyl, cyclobutyl, cyclopentyl, cyclohexyl, 1-methylcyclopropyl, 1-methylcyclobutyl, 1-methylcyclopentyl, 1-methylcyclohexyl, and an adamantyl group.

6. The method of claim 2 wherein $R_1$ is an arylalkyl group selected from phenylmethyl, 4-chlorophenylmethyl, 4-methoxyphenylmethyl, 4-nitrophenylmethyl, 2-(4'-nitrophenyl)ethyl, and a 3-(4'-nitrophenyl)propyl group.

7. The method of claim 2 wherein $R_1$ is selected from an aryloxyalkyl group is phenoxy-methyl, 4-nitrophenoxymethyl, 2-(4-nitrophenoxy)ethyl, 3-(4-nitrophenoxy)-propyl, 2,4-di-t-pentylphenoxymethyl, 1-(2,4-di-t-pentylphenoxy)propyl, 1-(2,4-di-t-pentylphenoxy)pentyl, 3-pentadecylphenoxymethyl, 1-(3-pentadecyl-phenoxy)propyl, 1-(4-butylsulfonylaminophenoxy)tridecyl, and a 2-octylsulfonylaminophenoxymethyl group.

8. The method of claim 2 wherein $R_1$ is selected from an alkylsulfonylalkyl group is 1-do-decylsulfonylpropyl, 3-dodecylsulfonylpropyl, 1-dodecylsulfonylpentyl, 1-dodecylsulfonyl-2-methypropyl, 1-tetradecylsulfonylpropyl, and a 1-hexadecylsulfonyl-propyl group.

9. The method of claim 2 wherein $R_1$ is selected from an arylsufonylalkyl group is 1-(4-do-decyloxybenzenesulfonyl)propyl, and 1-(4-hexadecyloxybenzenesulfonyl)propyl group.

10. The method of claim 2 wherein an aryl group is phenyl, 4-chloro-phenyl, 2-methoxyphenyl, 4-methoxyphenyl, 4-nitrophenyl, 4-dodecyloxyphenyl, or 4-hexadecyloxyphenyl.

11. The method of claim 2 wherein $R_1$ is selected from a heteroaryl 2-furyl, 3-pyridyl, or 3-quinolinyl group.

12. The method of claim 1 wherein $R_2$ is a substituted alkyl, aryl, or heteroaryl group having 1-30 carbon atoms.

13. The method of claim 12 wherein $R_2$ is a substituted alkyl that comprises a chloro-methyl, 1-bromopropyl, 1-bromopentyl, 1-bromo-2-methylpropyl, 1-bromo-tridecyl, nitromethyl, cyanomethyl, 4-nitrophenylmethyl, 4-nitrophenylpropyl, 4-nitrophenoxyymethyl, 1-(4-nitrophenoxy)propyl, 1-(4-nitrophenoxy)pentyl, 1-(4-nitrophenoxy)-2-methylpropyl, 1-(4-nitrophenoxy)tridecyl, 1-(4-butylsulfonylaminophenoxy)tridecyl, 3-(4-nitrophenoxy)propyl, 2-phthalimidoethyl, 1-methyl-2-phthalimidoethyl, ethoxycarbonylmethyl, 1-dodecylsulfonylpropyl, 1-dodecyl-sulfonyl-2-methylpropyl, 1-tetradecylsulfonylpropyl, 1-hexadecylsulfonylpropyl, 1-(4-dodecyloxyphenylsulfonyl)propyl, 1-(4-hexadecyloxyphenylsulfonyl)propyl, or a 2-octylsulfonylaminophenoxymethyl group.

14. The method of claim 12 wherein $R_2$ is a substituted aryl group that comprises a 2-nitrophenyl, 3-nitrophenyl, 4-nitrophenyl, 4-chloro-3-nitrophenyl, 2-butoxy-5-nitrophenyl, 4-ethoxycarbonylphenyl, 3-do-decyloxyphenyl, 4-dodecyloxyphenyl, 4-tetradecyloxyphenyl, 4-hexadecyloxy-phenyl, or a 2-(4-t-butylphenoxy)-5-nitro-phenyl group.

15. The method of claim 12 wherein $R_2$ is a substituted heteroaryl group that comprises a 5-nitro-2-furyl, 2-butoxy-3-pyridyl, or 5-nitro-3-pyrazolyl group.

16. The method of claim 1 wherein $R_1$ is a-butyl group and $R_2$ is 3-nitrophenyl group.

17. The method of claim 1 wherein $R_1$ is a t-butyl group and $R_2$ is 4-nitrophenyl group.

18. The method of claim 1 wherein $R_1$ is t-butyl group and $R_2$ is 1-phthalimido-2-propyl group.

19. The method of claim 1 wherein $R_1$ is t-butyl group and $R_2$ is 4-nitrophenoxy-propyl group.

20. The method of claim 1 wherein $R_1$ is methyl group and $R_2$ is 3-nitrophenyl group.

21. The method of claim 1 wherein $R_1$ is p-methoxyphenyl group and $R_2$ is 3-nitrophenyl group.

22. The method of claim 1 wherein the reaction uses 1.05-2.5 eq. of hydrazine.

23. The method of claim 1 wherein the reaction is carried out at 25-200° C.

24. The method of claim 1 wherein the reaction is carried out in an organic solvent or solvent mixture.

25. The method of claim 24 wherein the organic solvent comprises an alcoholic solvent, hydrocarbon solvent, ethereal solvent, ester, organic acid, or organic base.

26. The method of claim 25 wherein the organic solvent comprises an alcoholic solvent selected from methanol, ethanol, propyl alcohol, isopropyl alcohol, and n-butyl alcohol.

27. The method of claim 25 wherein the organic solvent comprises a hydrocarbon solvent selected from hexane, heptane, toluene, and xylene.

28. The method of claim 25 wherein the organic solvent is an ethereal solvent selected from di-isopropyl ether, tetrahydrofuran, and dioxane.

29. The method of claim 25 wherein the organic solvent is an ester selected from ethyl acetate, propyl acetate, and ethyl propionate.

30. The method of claim 25 whereinthen organic acid is formic acid, acetic acid, propionic acid, or methanesulfonic acid.

31. The method of claim 25 wherein the organic base is pyridine, N,N-di-methylaniline, triethylamine, or triehtanolamine.

32. The method of claim 1 wherein the reaction runs without an acid catalyst.

33. The method of claim 1 wherein the reaction runs with an acid catalyst.

34. The method of claim 33 wherein an acid catalyst is hydrochloric acid, sulfuric acid, phosphoric acid, formic acid, acetic acid, propionic acid, methanesulfonic acid, benzenesulfonic acid, or p-toluenesulfonic acid.

* * * * *